(12) United States Patent
Dave et al.

(10) Patent No.: US 6,756,217 B1
(45) Date of Patent: Jun. 29, 2004

(54) GLASS COMPOSITE MATERIALS CONTAINING ALKOXOSILANE DERIVATIVE HAVING ALTERABLE CHARGE, HYDROPHOBIC AND HYDROPHILIC GROUPS

(75) Inventors: Bakul C. Dave, Carbondale, IL (US); Mukti S. Rao, Evanston, IL (US)

(73) Assignee: Southern Illinois University, Carbondale, IL (US)

( * ) Notice: Subject to any disclaimer, the term of this patent is extended or adjusted under 35 U.S.C. 154(b) by 0 days.

(21) Appl. No.: 09/320,793

(22) Filed: May 27, 1999

Related U.S. Application Data

(60) Provisional application No. 60/087,165, filed on May 29, 1998.

(51) Int. Cl.[7] .......................... C12N 11/14; C12M 1/00; A61K 9/00; G01N 33/552; C07K 17/14
(52) U.S. Cl. ...................... 435/176; 424/400; 424/484; 435/4; 435/177; 435/283.1; 435/287.1; 435/289.1; 435/803; 436/527; 530/412; 530/811
(58) Field of Search .......................... 435/4, 176, 177, 435/283.1, 287.1, 289.1, 803; 436/524, 527; 530/412, 811; 424/484, 400

(56) References Cited

U.S. PATENT DOCUMENTS

| | | | | | |
|---|---|---|---|---|---|
| 4,418,195 A | * | 11/1983 | Quinlan | ..................... | 544/58.2 |
| 5,077,210 A | * | 12/1991 | Eigler et al. | ................. | 435/176 |
| 5,200,334 A | * | 4/1993 | Dunn et al. | ................. | 435/182 |
| 6,080,402 A | * | 6/2000 | Reetz et al. | ................ | 424/94.6 |
| 6,090,399 A | * | 7/2000 | Ghosh et al. | ................ | 424/409 |
| 6,235,864 B1 | * | 5/2001 | Loy et al. | ...................... | 528/35 |
| 6,258,914 B1 | * | 7/2001 | Su et al. | ....................... | 528/15 |
| 6,440,711 B1 | * | 8/2002 | Dave | ......................... | 435/157 |

* cited by examiner

*Primary Examiner*—David M. Naff

(57) ABSTRACT

A porous glass composite material is prepared comprising a gel containing water and a polymeric network containing at least one alkoxosilane derivative having a group of alterable charge, a hydrophobic group and a hydrophilic group. The alkoxosilane derivative is preferably a derivative of an alkoxosilane having the general formula $(OR^1)_3Si$-spacer-$Si(OR^2)_3$, wherein $R^1$ and $R^2$ are the same or different and may be hydrogen; substituted and unsubstituted, branched and unbranched $C_{1-20}$-alkyls; substituted and unsubstituted, branched and unbranched $C_{1-20}$-alkenyls; substituted and unsubstituted, branched and unbranched $C_{1-20}$-alkynyls; substituted, unsubstituted, and multiple ring aryl groups; or combinations thereof; and water. Devices including the glass composite include chromatographic and other separation media, drug delivery vehicles, and electric and mechanical actuators.

36 Claims, 13 Drawing Sheets

(7 of 13 Drawing Sheet(s) Filed in Color)

Pore-Size Engineering
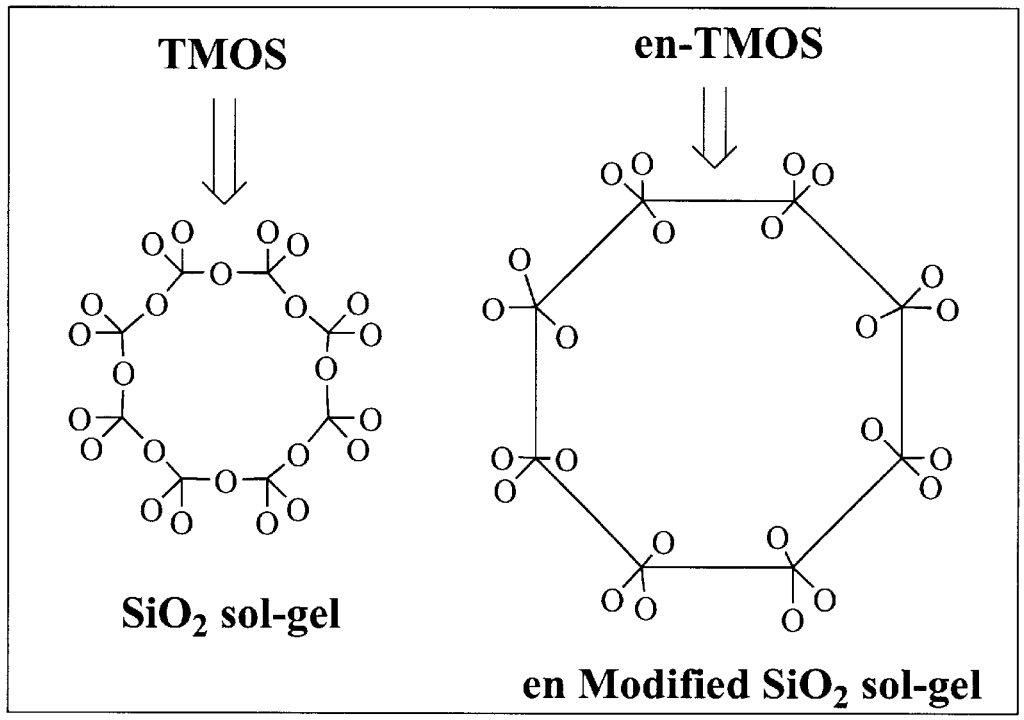
Fig.1a shows the enlargement of pores in the enTMOS gel in comparison to TMOS due to the inclusion of the rigid organic spacer group.
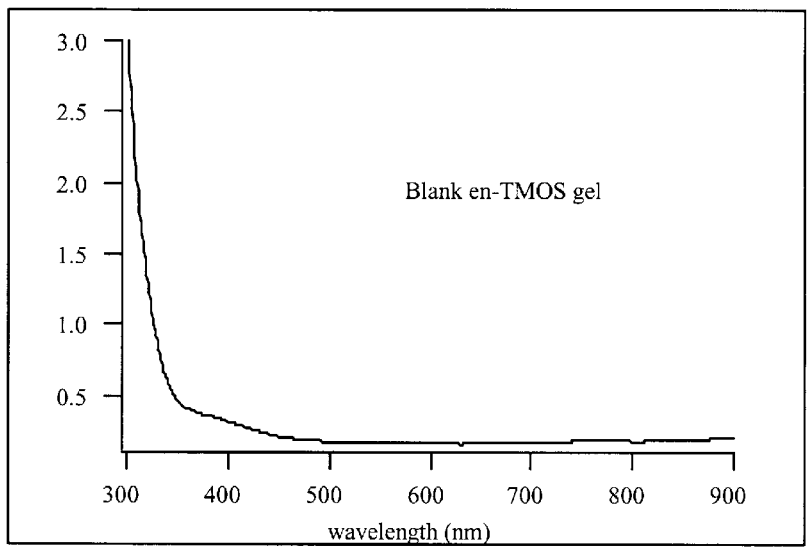
Fig.1b shows a tail in the yellow region ~ 380-400nm indicating the enlargement of pores.

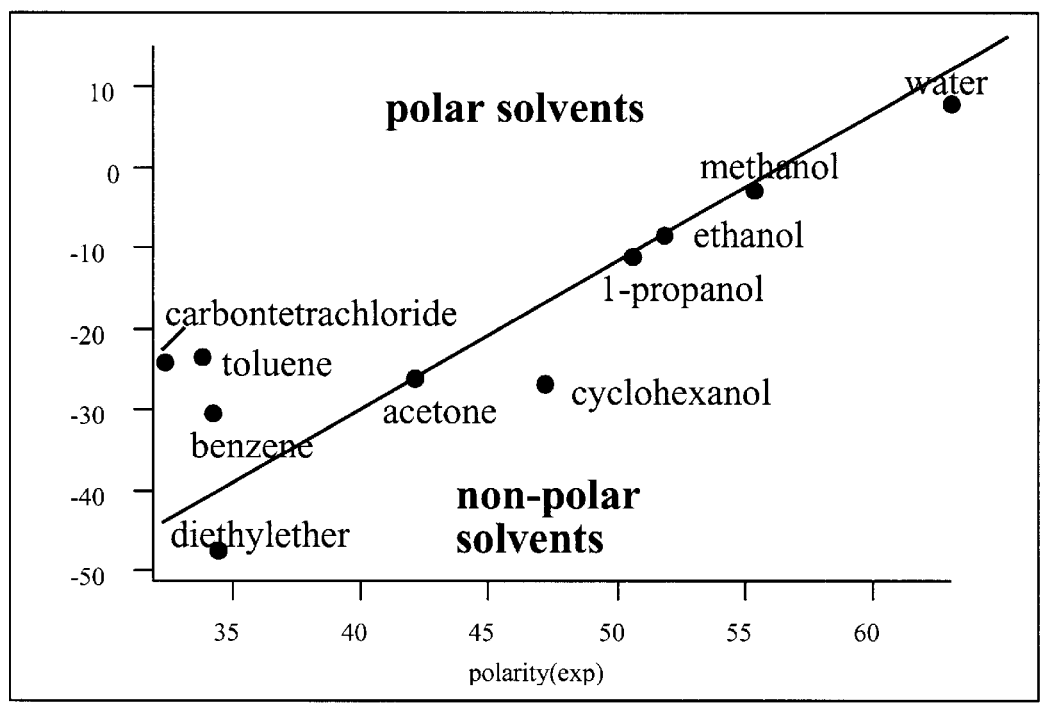
Fig.2 shows an increased % weight change in enTMOS gel in polar solvents as compared to non polar solvents.

Thermomechanical Response of enTMOS gels
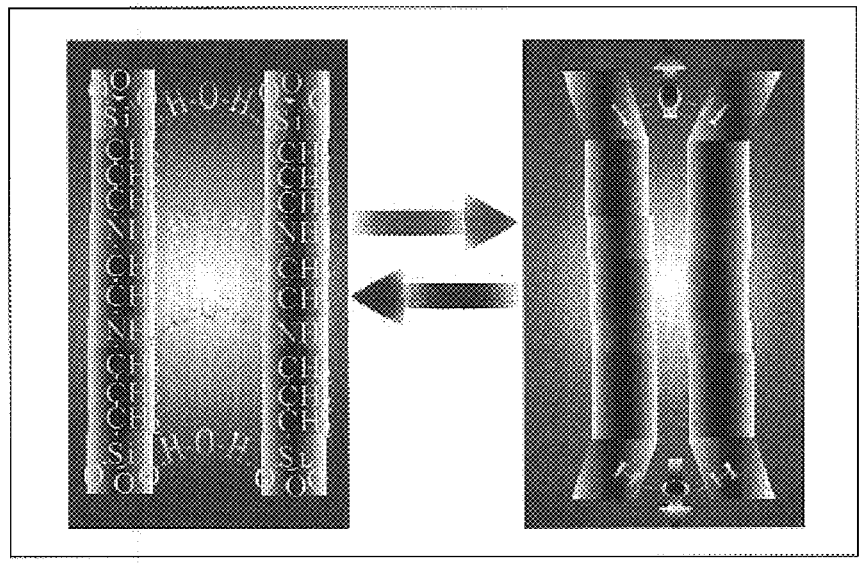
Fig.3a shows a reversible temperature dependent hydration-dehydration of the enTMOS gel, resulting in increased hydrophobicity at higher temperatures.
Thermomechanical Effect
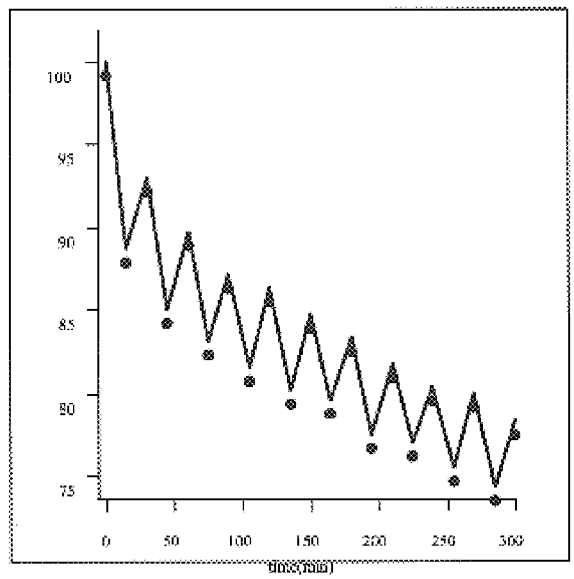
Fig.3b shows a temperature dependent reversible % weight change in enTMOS gel with time.

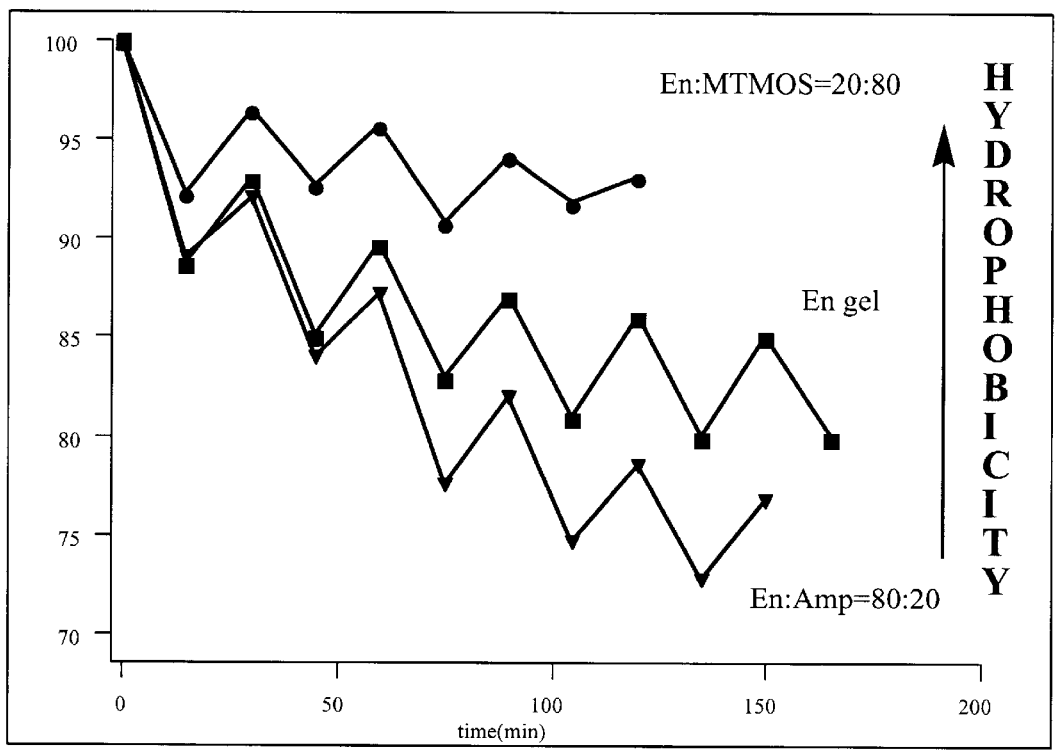
Fig.4 shows an increased % weight change in a material with greater hydrophilic composition than enTMOS and a decreased % weight change in a material with an increased hydrophobic composition.

Stability of Biomolecules in enTMOS Gel
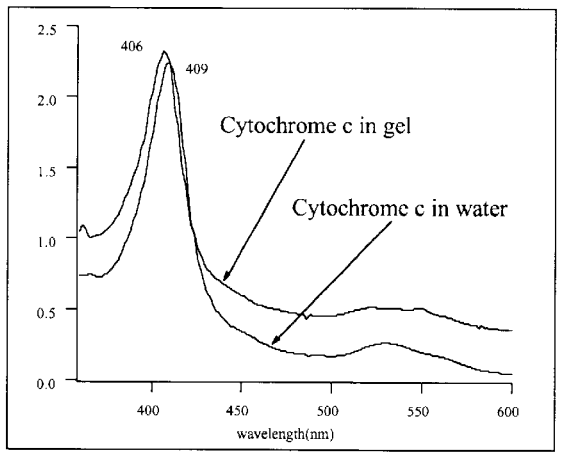
Fig. 5a shows the stability of Cyt*c* in enTMOS gel.
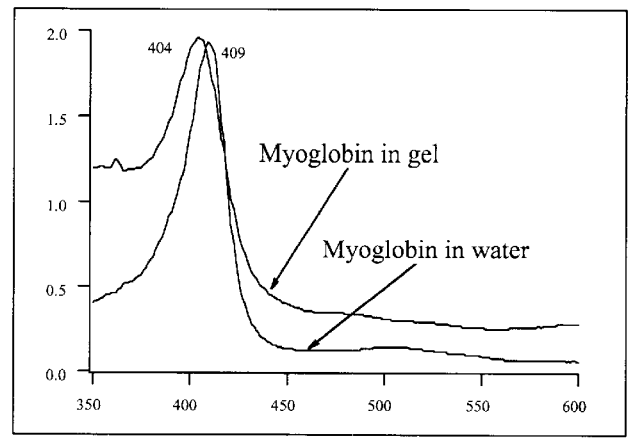
Fig. 5b shows the stability of Mb in enTMOS gel.

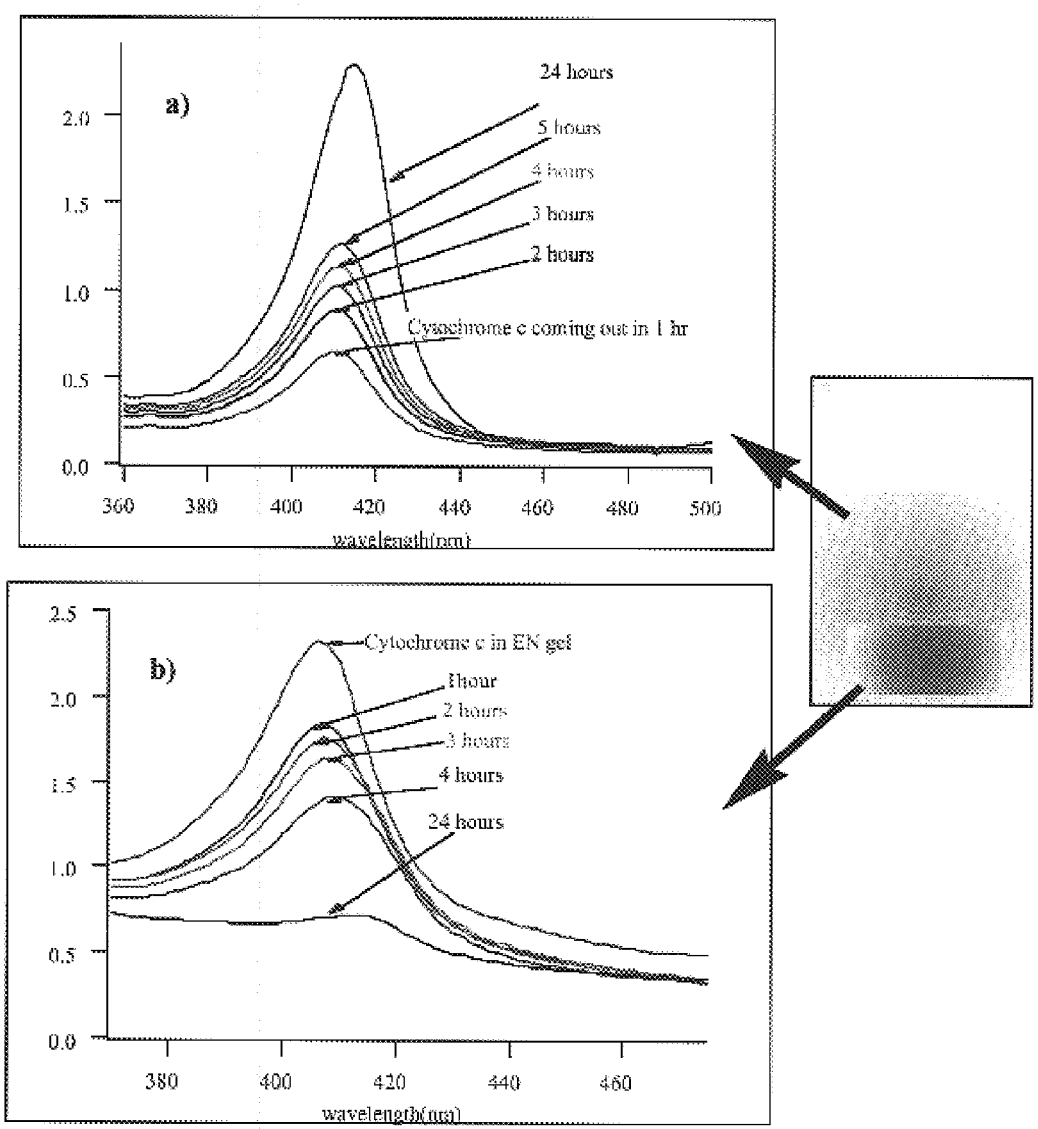
Fig. 6 a) shows the release of Cyt c with time from the enTMOS gel in acetate solution. b) shows the release of Cyt c with time from the enTMOS gel.

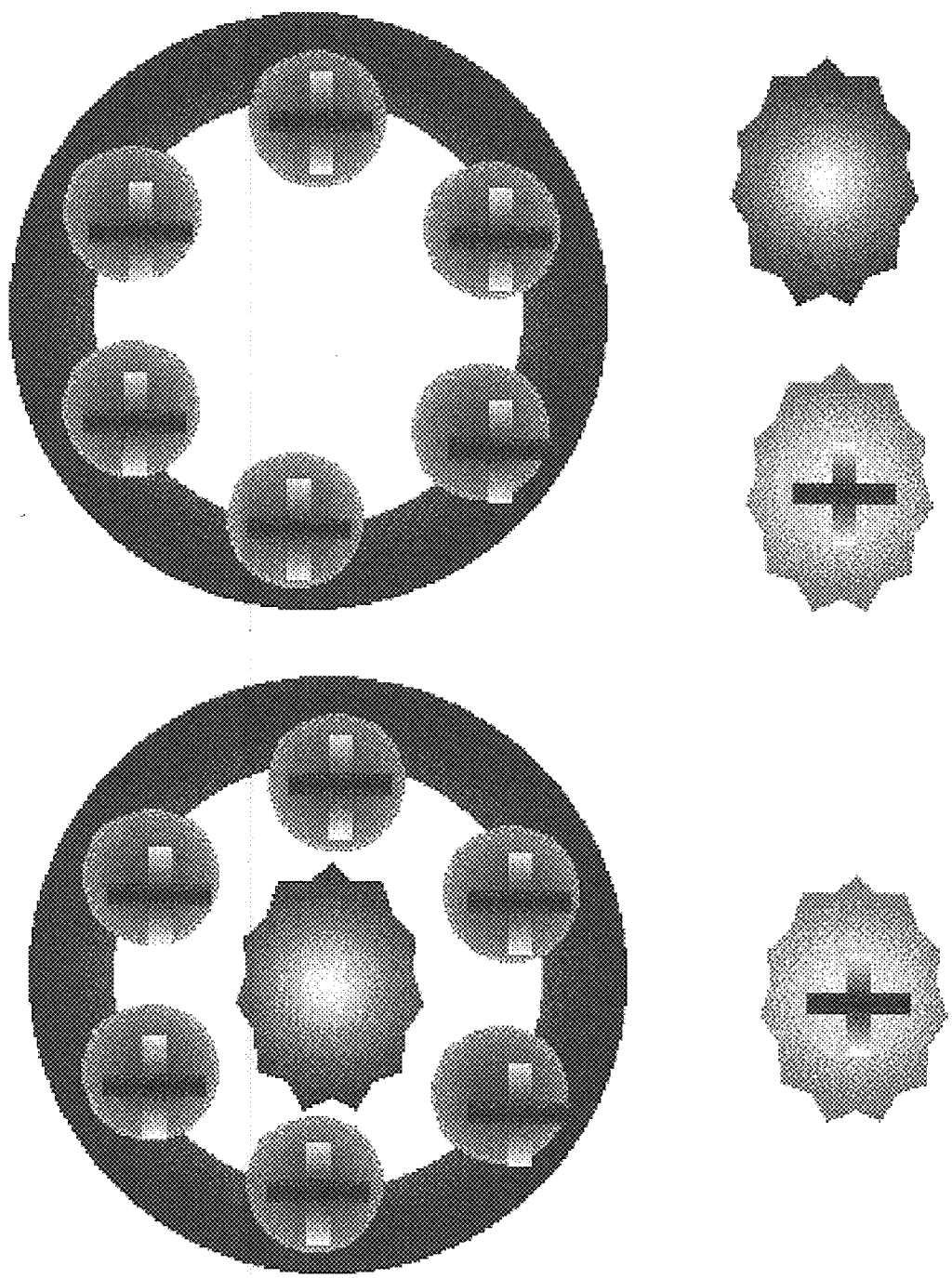
Fig.7 The positively charged enTMOS gel selectively picks up Mb/Hb (+2 charged) in comparison to Cyt c (+8 charged), from a mixture of Cyt c and Mb/Hb.

Separation of Biomolecules: Myoglobin and Cytochrome c
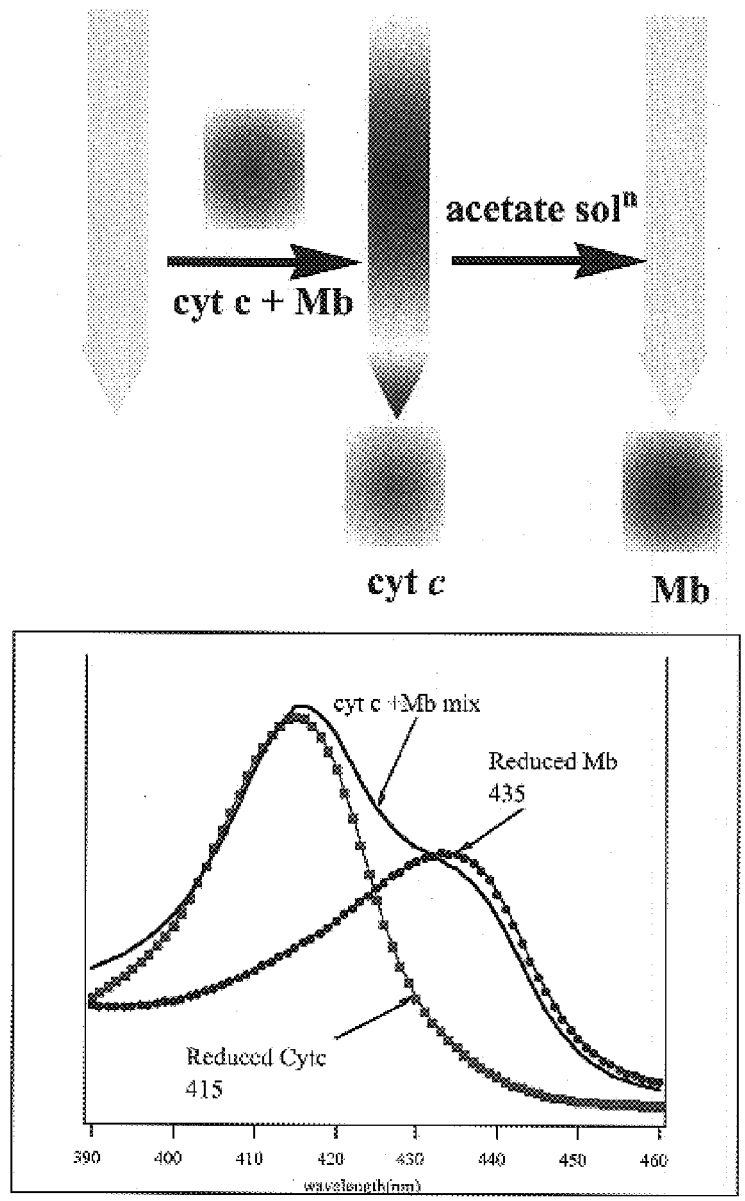
Fig.8 The curves show the separation of Cytc and Mb after their mixture was passed through the column containing enTMOS gel in powdered form. Cytc comes out first, followed by Mb which is eluted with acetate solution.

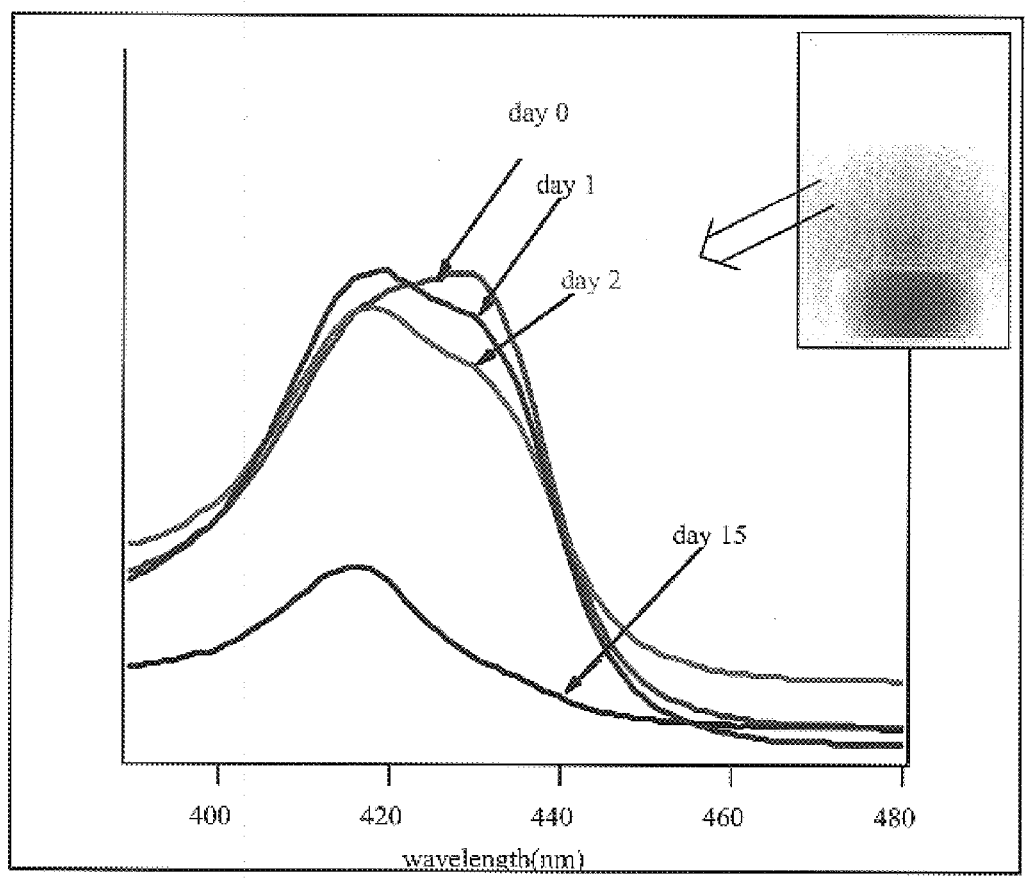
Fig.9 Monitoring the solution of Cyt $c$ and Hb in contact with the enTMOS gel shows an increase in the ratio of Cyt $c$ /Hb, indicating a selective intake of Hb over Cyt $c$ by enTMOS gel.

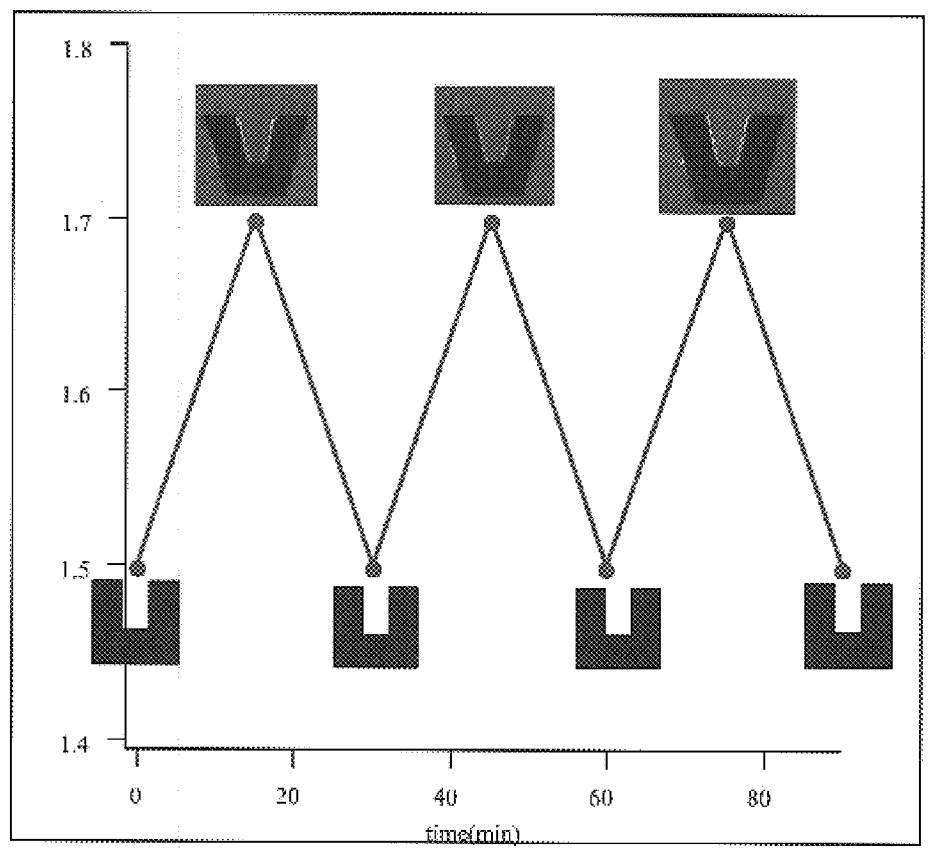
Fig.10 shows a reversible electromechanical response of enTMOS tweezers with an applied potential of 6V.

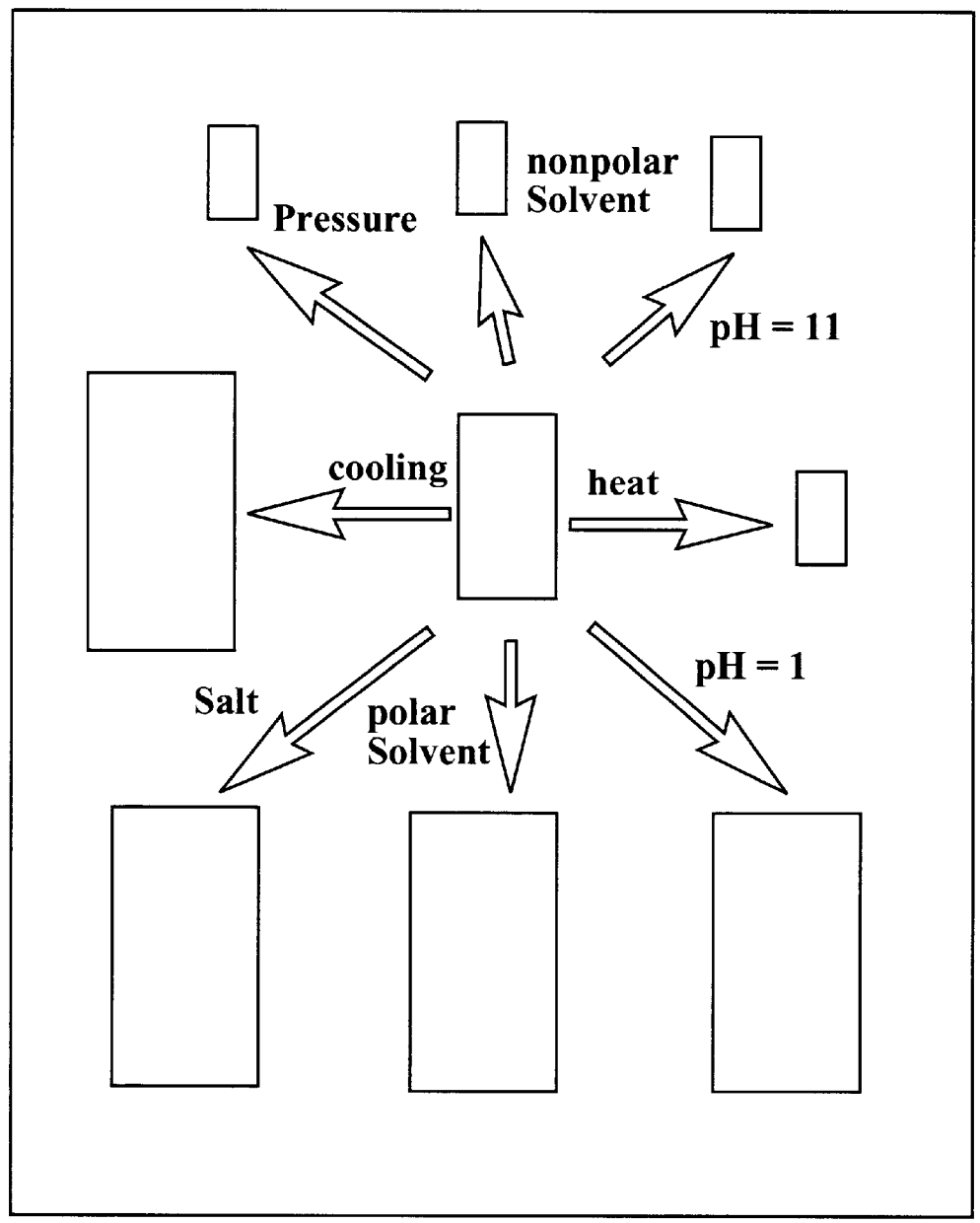
Fig.11 shows the influence of various environmental stimuli on enTMOS gel.

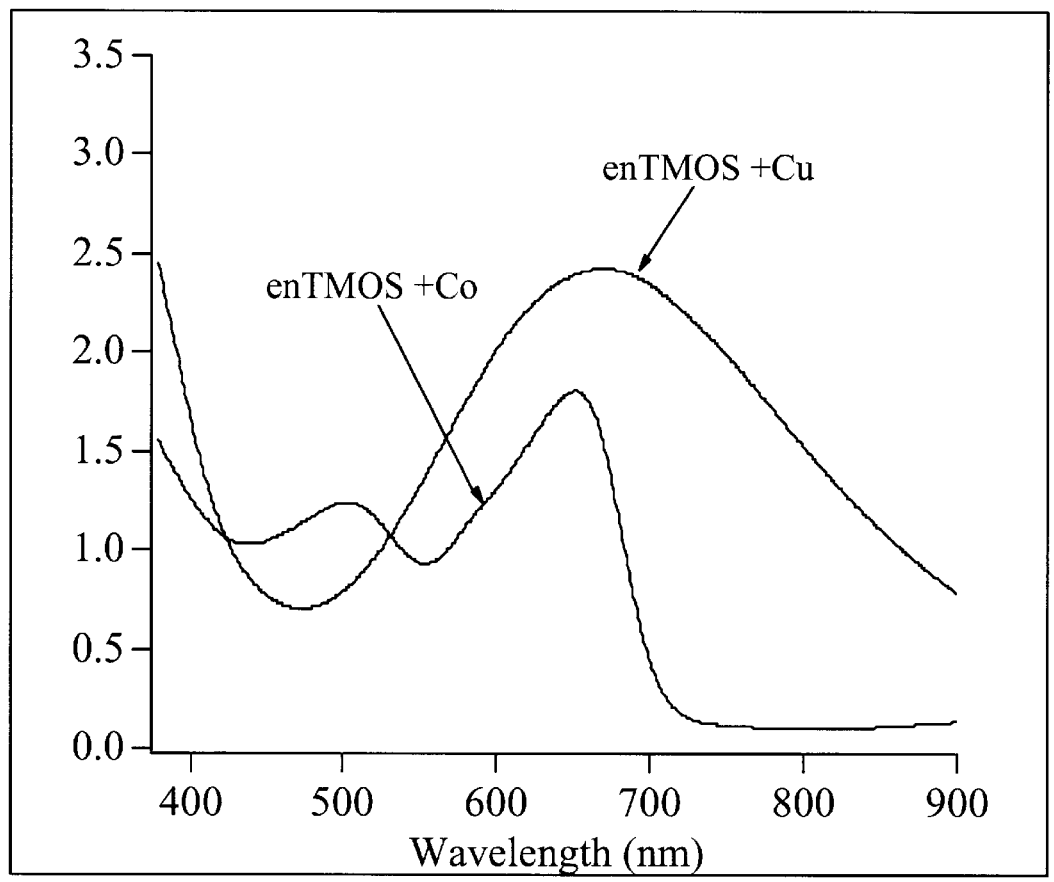
Fig. 12 shows the intake of $Cu^{2+}$ and $Co^{2+}$ ions by enTMOS gel enTMOS
Microelectromechanical Devices
● Shape Memory
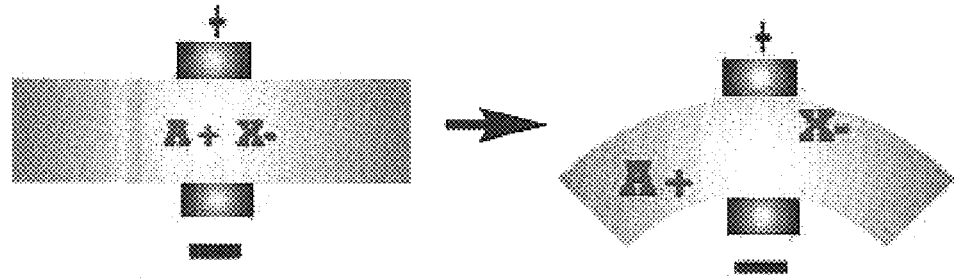
● Microtweezers
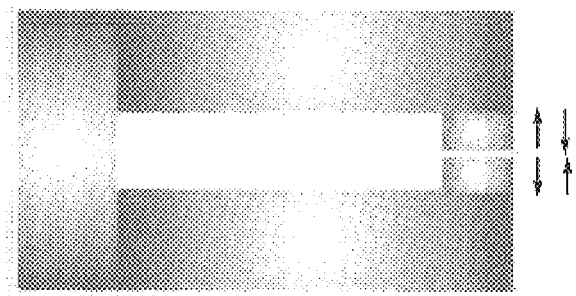
● Microsyringe / Micropump
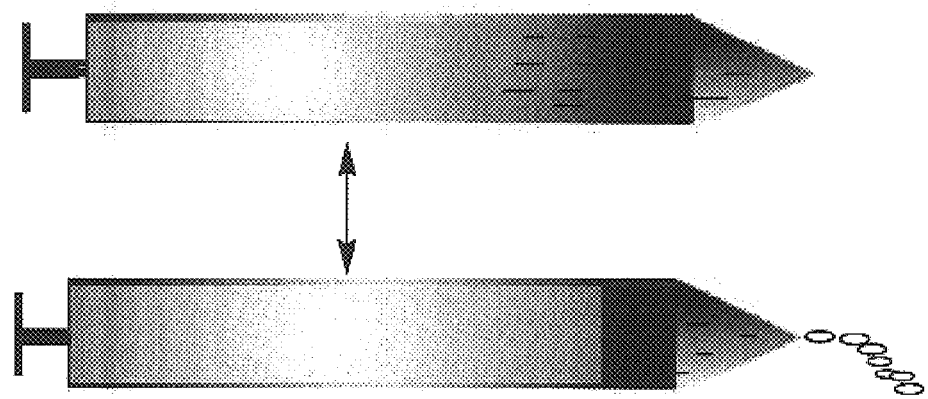
Fig.13 shows the practical devices that can be made out of enTMOS gel.

GLASS COMPOSITE MATERIALS CONTAINING ALKOXOSILANE DERIVATIVE HAVING ALTERABLE CHARGE, HYDROPHOBIC AND HYDROPHILIC GROUPS

PRIORITY APPLICATION INFORMATION

This application is a regular United States patent application under 37 C.F.R. §1.111(a) based on and claiming priority to U.S. Provisional Application Serial No. 60/087,165 filed May 29, 1998, the entire contents of which are herein incorporated by reference.

TECHNICAL FIELD

The present invention relates generally to composite materials that react to stimuli from the environment in which they are placed. Such materials are generally referred to as "smart" materials. More particularly, then, the present invention relates to environmentally sensitive "smart" glass composite materials.

BACKGROUND ART

A continuing aim of current science and technology is to mimic nature for assembly of different functional materials, with synthetic control at the molecular level. Natural systems are extremely efficient, and perform to their optimum under very mild conditions. Thus, a new scientific-technical field has developed around artificial "molecular mechanical systems", as suggested by Osada et al. (1993) *Progress in Polymer Science*, 18:187–226. Such systems are structural-functional assemblies which convert energy from one form to another through changes in the structure or function. It is therefore desirable but somewhat problematic, to synthesize such materials with precise control at a molecular level such that changes in structure or structural interactions can cause an energy difference, resulting in a function or movement of the molecular mechanical system or assembly. Such molecular mechanical systems or assemblies have application in micro- and macro-intelligent systems, in controlled drug release, as artificial implants, as optical shutters, in molecular separation systems, and the like.

As pointed out by Osada (May 1993) *Scientific American*, pp. 82–87, unlike natural materials, which are usually soft and wet, most industrial materials like metals, ceramics and plastics are dry and hard and so, cannot be used to make soft, bio-mimetic, and flexible materials. One class of materials, polymer gels, comes closer to natural systems in terms of soft-wet character. Polymer gels usually include an elastic, three dimensionally cross-linked network (provided by covalent bonds, physical entanglements, hydrogen bonding, Van der Waals forces, or hydrophobic interactions), and a fluid filling the interstitial space in the network. Their mechanical characteristics, optical properties, surface properties, sorption capacities, degree of swelling, etc., give them the ability to adapt to changes in their environment, thereby making them useful for various applications. Such materials that are capable of sensing a change in their environment and responding to them by altering one or more of their property coefficients are termed as "smart materials". Gehrke, S. H. (1993) *Advances in Polymer Science*, 110:80–144 states that this "smart" ability can be finely tuned for a wide variety of applications, including switches, sensors, electromechanical-chemomechanical actuators, drug delivery devices, recyclable absorbents, specialized separation systems, bioreactors, bioassay systems, artificial muscles and display items, including light emitting diodes (LEDs), TV monitors, and the like.

The polymeric backbone of the polymer gel can be an organic or an inorganic network containing functional groups that are ionizable, amenable to red-ox reactions, photoactive, or capable of swelling by reversibly exchanging monovalent and divalent ions, as stated by Rossi et al. (1992) *Journal of Intelligent Material System and Structure* 3:75–95. The polymeric network can thus generate force by swelling or shrinking; or can undergo a reversible change in its volume in response to a change in its environment, temperature, solvent composition, mechanical strain, electric field, exposure to light, or the like, with no inherent limits in lifetime.

Extensive work has been done, and continues to be done with organic polymer gels having a hydrocarbon backbone which comprises a variety of functional groups, including -amine, -hydroxy, -amide, and -carboxyl. Gehrke, S. H. (1993) *Advances in Polymer Science*, 110:80–144 described the synthesis of organic polymer gels by techniques including co-polymerization/cross-linking of monomers, cross-linking of linear polymers by treatment with chemicals or gamma ($\gamma$) radiation, and chemical conversion of one gel type to another.

Polymers made out of a single monomer have been used in a number of applications. For example, a neutral polymer gel of poly(vinyl alcohol) with water as a mobile component has been shown to undergo swelling, and to perform the mechanical work of lifting a load. Additionally, poly (silamine) telechelic oligomers, consisting of alternating 3,3-dimethyl-3-silapentane and N,N-diethylene units have been synthesized for use as high performance stimulus-sensitive materials, and as a poly(silamine) brush on glass and gold surfaces, as described by Nagasaki (March 1997) *ChemTech*, 23–29.

One of the most intensively studied responsive polymer gels has been cross-linked poly(N-isopropylacrylamide) (PNIPAAm). A number of environmental stimuli, including solvent, pH, temperature, electric fields, or electromagnetic radiation have been used to collapse or swell hydrogels made out of PNIPAAm, for use in various applications.

For example, PNIPAAm polymer gels were used by Feil et al. (July 1991) *Journal of Membrane Science*, 64:283–294 in molecular separation by thermosensitive membranes. PNIPAAm hydrogel membranes have been used to separate dextrans of molecular weights of 150,000 and 4,400 g/mol, respectively; and to separate uranine of molecular weight of 376 g/mol. The swelling characteristics can be influenced by an appropriate hydrophobic/hydrophilic balance in the hydrogel. Thus, this ratio has been used to vary the degree of swelling of these membranes. Such hydrogels also demonstrated a negative thermosensitivity, with the material showing dehydration at high temperature induced by hydrophobic interactions in the hydrogel. Thus, the hydrogel swelled under low temperature conditions and shrunk at higher temperatures. These swelling characteristics provided for permeability of the small molecules (uranine) at all temperatures (–27° C.), followed by the 4,400 dextran at 23° C., and the 150,000 dextran at less than 20° C., thereby achieving separation of a mixture of molecules having a distinct difference in molecular size.

PNIPAAm hydrogels were characterized by Hoffman et al. (1986) *Journal of Controlled Release* 4:213–222 as thermally reversible hydrogels. Particularly, PNIPAAm hydrogels have been observed to show, at a fixed pH, reversible shrinking and expansion at 50° C. and 4° C., respectively. The shrinking and expansion provides for the releasing and absorbing of biomolecules, including myoglobin and vitamin B 12; and organic molecules, including Methylene Blue.

PNIPAAm hydrogels have also been applied as comb-type grafted hydrogels with rapid de-swelling response to temperature changes, as described by Yoshida et al. (Mar. 16, 1995) *Nature* 374:240–242. Hydrogels made of PNIPAAm with a comb structure undergo changes in volume in response to external stimuli like temperature. They collapse from their hydrated form to dehydrated form with increasing temperature because of hydrophobic interactions between the polymeric network.

PNIPAAm hydrogels have also been utilized in the synthesis and application of modulated polymer gels, as described by Hu et al. (July 1995) *Science* 269:525–527. Polymeric gels made of polyacrylamide interpenetrated by NIPAAm network have been made into a bagel strip, a shape memory gel, and a gel "hand". Each of these structures respond to environmental changes, such as change in temperature or change in acetone concentration.

To modify the properties of PNIPAAm polymers so as to tune their applicability, they have been co-polymerized with different monomers. For example, thermally responsive polymers for drug permeation and release have been described by Okano et al. (1990) *Journal of Controlled Release* 11:255–265. Polymers of PNIPAAm cross-linked with butyl-methacrylate and interpenetrating networks of polytetramethyleneetherglycol (PTMEG) show shrinking with increasing temperature. Particularly, the surface of the membrane shrinks, rather than the bulk, thereby regulating water and solute movement. The release of indomethacin (a model drug) has been studied with this system. At low temperatures, the release of the drug from the polymer followed a pseudo zero order or first order kinetics, and at higher temperatures, it failed to diffuse out.

Dong et al. (1990) *Journal of Controlled Release* 13:21–31 state that thermally, reversible hydrogels made for PNIPAAm and bis-vinyl terminated polydimethylsiloxane (VTPDMS) show swelling-shrinking behavior with respect to temperature and solvents. The gels swell in water and ethanol, permitting loading of hydrophilic and hydrophobic drugs at 25° C., and subsequent release in ethanol-water mixture at 37° C.

Polymeric systems of 2-hydroxyethyl methacrylate and ethyleneglycol dimethacrylate, and poly(vinyl alcohol) cross-linked with glutaraldehyde were used to prepare hydrogel beads for oral drug delivery as described by Kim et al. (August 1994) *ChemTech* pp. 36–39. Similar polymers have been used to make contact lenses, and have been used in implantation and transplantation surgery other than the controlled drug release systems, as described in Rossi et al. (1992) *Journal of Intelligent Material System and Structure* 3:75–95.

Despite the intensive study of organic polymer gels like cross-linked poly(N-isopropylacrylamide) (PNIPAAm), there are many problems that limit application of such polymer gels as "smart" materials. For example, time consuming, multi-step synthesis processes which produce low yields and require harsh conditions unsuitable for the encapsulation of biomolecules must be utilized to synthesize the organic polymer gels. In addition, the synthesis of organic polymers require large amounts of precursors and other chemicals, which raises the overall cost of manufacture. The encapsulation of biological molecules in the organic polymers must be carried during post-synthesis steps, as the high temperatures that are required for preparation of these polymers are incompatible with biological molecules. Thus, the complexity of the overall process increases. Moreover, organic polymeric materials require presence of organic solvents for swelling/shrinkage, and therefore usage in biomedical drug delivery applications is, to a large extent, precluded. Therefore, there is a continuing need in the art for alternative materials to organic polymeric gels for application as "smart" materials.

One of the art-recognized methods of making inorganic polymeric gels with soft and wet characteristics is by the use of a sol-gel. Other art-recognized methods include solid-state reaction, melt-quenching, and vapor phase deposition methods. The sol-gel process utilizes mild synthesizing conditions, and thus offers flexibility in material design and synthesis at a molecular level. Particularly, Hench et al. (1990) *Chemical Reviews* 33–72 describe the sol-gel process as a process of making a three dimensional M-O-M polymeric network by hydrolysis and condensation process of appropriate alkoxy precursors. The reactions are generally described as follows:

| Hydrolysis: | | -MOR + $H_2O$ → -MOH + ROH |
| Condensation: | | -MOH + ROM → -MOM- + ROH |
| | Or | -MOH + HOM → -MOM- + $H_2O$ |

Thus, the factors which affect either or both of the above reactions are likely to have an impact on the properties of the gel. Faster hydrolysis and slower condensation results in small pore sized gel and slower hydrolysis and faster condensation result in bigger pore sized gel. If M is a silicon atom, then a Si—O—Si network, i.e., a glass-like material, is produced at room temperature.

Inorganic sol-gel materials have also been used to make chemical and biochemical sensors by encapsulating various kinds of organic and biomolecules as described by Dave et al. (1994) *Analytical Chemistry* 66:1120A–1127A. They have also been used to make electrochromic, photochromic, and thermochromic materials, i.e., change in color of the material with respect to changes in an electric field, temperature, respectively, etc., as described by Agerter (1996) *Structure and Bonding* 85:149–194.

Despite the existence of various prior art "smart" materials having organic or inorganic polymer backbones, there remains much room for improvement in the art. Specifically, there exists a continuing need for improved "smart" materials that are relatively simple to synthesize and yet provide desirable levels of sensitivity to particular environmental stimuli.

SUMMARY OF THE INVENTION

A porous glass composite material comprising at least one alkoxodisilane precursor and water is disclosed. The at least one alkoxodisilane precursor has the general formula $(OR^1)_3Si\text{-spacer-}Si(OR^2)_3$, where $R^1$ and $R^2$ may be the same or different and may comprise hydrogen, alkyl, alkenyl, alkynyl, or aryl groups. The two silicon atoms are bridged by a spacer unit comprising an organic unit, an inorganic unit, biological unit and/or combinations thereof.

Optionally, the glass composite material of the present invention may further comprise an acid or base catalyst. The glass composite material of the present invention may further comprise an additive associated with imparting a desired functional property to the glass composite material.

An article of manufacture or a device comprising the glass composite material of the present invention is also disclosed herein. Examples of such articles and devices include chromatographic and other separation media, microsyringes, micropumps, delivery vehicles for bioactive molecules, and electric and mechanical actuators.

Accordingly, it is an object of the present invention to provide an improved glass composite material having environmentally sensitive or "smart" characteristics.

It is another object of the present invention to provide an improved glass composite "smart" material that is easy to synthesize as compared to prior art synthesis methods of organic polymer "smart" materials.

It is yet another object of the present invention to provide an improved glass composite "smart" material that possesses large pores that enhance "smart" characteristics.

It is a further object of the present invention to provide an improved glass composite "smart" material suitable for use in fabricating a variety of devices and articles of manufacture.

It is still a further object of the present invention to provide an improved glass composite "smart" material that is suitable for encapsulation of biologically derived materials or bioactive molecules, such as drugs.

Some of the objects of the invention having been stated hereinabove, other objects will become evident as the description proceeds, when taken in connection with the accompanying Drawings and Laboratory Examples as best described hereinbelow.

BRIEF DESCRIPTION OF THE DRAWINGS

This appln has at least one drawing executed in color.

FIG. 1a is a structural schematic showing enlargement of pores in the enTMOS gel in comparison to TMOS due to the inclusion of the rigid organic spacer group;

FIG. 1b is a graph showing a tail in the yellow region ~380–400 nm indicating the enlargement of pores;

FIG. 2 is a graph showing an increased % weight change in enTMOS gel in polar solvents as compared to nonpolar solvent;

FIG. 3a is a schematic showing a reversible temperature-dependent hydration/dehydration of the enTMOS gel, resulting in increased hydrophobicity at higher temperatures;

FIG. 3b is a graph showing a temperature-dependent reversible % weight change in enTMOS gel with time;

FIG. 4 is a graph showing an increased % weight change in a material with greater hydrophilic composition than enTMOS and a decreased % weight change in a material with an increased hydrophobic composition;

FIG. 5a is a graph showing the stability of Cyt c in enTMOS gel;

FIG. 5b is a graph showing the stability of Mb in enTMOS gel;

FIG. 6a is a graph showing the release of Cyt c with time from the enTMOS gel in acetate solution;

FIG. 6b is a graph showing the release of Cyt c with time from the enTMOS gel;

FIG. 7 is a schematic showing that the positively charged enTMOS gel selectively picks up Mb or Hb (+2 charged) in comparison to Cyt c (+8 charged), from a mixture of Cyt c and Mb or Hb;

FIG. 8 is a schematic showing the curves illustrating the separation of Cyt c and Mb after their mixture was passed through the column containing enTMOS gel in powdered form—Cyt c comes out first, followed by Mb, which is eluted with acetate solution;

FIG. 9 is a graph showing the monitoring of the solution of Cyt c and Hb in contact with the enTMOS gel illustrating an increase in the ratio of Cyt c/Hb, indicating a selective intake of Hb over Cyt c by enTMOS gel;

FIG. 10 is a schematic and a graph showing a reversible electromechanical response of enTMOS tweezers with an applied potential of 6V;

FIG. 11 is a schematic showing the influence of various environmental stimuli on enTMOS gel;

FIG. 12 is a graph showing the intake of $Cu^{(+2)}$ and $Co^{(+2)}$ ions by enTMOS gel; and FIG. 13 depicts practical devices that can be made out of enTMOS gel.

DETAILED DESCRIPTION OF THE INVENTION

The present invention is directed to the design and synthesis of a novel class of porous glass composite material that undergoes changes in structure with respect to environmental factors including, but not limited to temperature, pH, solvent, salt, metal ions, chemical species, mechanical pressure, electrical potential, light, ultrasonic sound, and other environmental factors. The materials are prepared by the sol-gel method using organically modified alkoxosilane precursors. The "smart" properties of the materials derive from the particular composition of the precursor. Therefore, according to the present invention, a novel glass composite material with predetermined functional properties is provided.

An alkoxosilane precursor covalently modified with, for example, a bridging Bis(propyl)ethylenediamine group results in the formation of a gel with a particular hydrophilic/hydrophobic composition, and bigger pore size than the parent $SiO_2$ gel. This makes the material hold more water, and hence, exhibit sharp changes in response to relatively small changes in temperature or pH. It can also lead to entrapment and controlled release of larger biomolecules and organic molecules. The presence of the amine group in the gel results in the gel coordinating to metal ions, hydrogen bonding with water and polar molecules, carrying different charges at different pH, i.e., being protonated or deprotonated at low or high pH, respectively. The presence of the hydrophobic groups provides the gel with more mechanical strength, rigidity, and thermal stability.

Thus, the present invention comprises a porous glass composite material comprising (1) at least one alkoxodisilane precursor having the general formula $(OR^1)_3$Si-spacer-Si$(OR^2)_3$, where $R^1$ and $R^2$ may be the same or different and may comprise hydrogen, alkyl, alkenyl, alkynyl, or aryl groups as defined herein below, and the two silicon atoms are bridged by a spacer unit comprising an organic unit, an inorganic unit, biological unit and combinations thereof; and (2) water. Examples of preferred spacer units include, but are not limited to, a charged functional group or domain; a hydrophobic domain; a hydrophilic domain; a functional group or domain having a moiety selected from a group including, but not limited to, —S, —N, —N=N—, halogen (—I, —Br, —F, —Cl), —OR, —R—O—R, —HOOCR, —HOR (where R=hydrogen, alkyl, alkenyl, alkynyl, or aryl as defined herein below, and R may be the same moiety or different moieties); and functional groups with variable ratios of charged, hydrophobic, and/or hydrophilic domains. Examples of more preferred spacer units include RHN(CH$_2$)$_2$NHR, RNHR, and RNHCON HR, where R=hydrogen, alkyl, alkenyl, alkynyl, or aryl as defined herein below, and R may be the same moiety or different moieties.

Within the definition of R generally and with respect to $R^1$ and $R^2$ in the general formula referenced above, the term "alkyl" is meant to have its art-recognized meaning. Substituted and unsubstituted, as well as branched and unbranched $C_1$ through $C_{20}$-alkyls are particularly contemplated, including methyl-, ethyl-, propyl-, isopropyl-, n-propyl- and butyl-. Exemplary substituents include —OH and —OR', wherein R' is a $C_{1-4}$ alkyl. Table 1 set forth below also describes contemplated alkyls.

Within the definition of R generally and with respect to $R^1$ and $R^2$ in the general formula referenced above, the term "alkenyl" is meant to have its art-recognized meaning. Substituted and unsubstituted, as well as branched and unbranched $C_1$ through $C_{20}$-alkenyls having at least one double bond at varying locations are particularly contemplated, including vinyl-, allyl- and isopropenyl-. Exemplary substituents include —OH and —OR', wherein R' is a $C_{1-4}$ alkyl. Table 1 set forth below also describes contemplated alkenyls.

Within the definition of R generally and with respect to $R^1$ and $R^2$ in the general formula referenced above, the term "alkynyl" is meant to have its art-recognized meaning. Substituted and unsubstituted, as well as branched and unbranched $C_1$ through $C_{20}$-alkynyls having at least one triple bond at varying locations are particularly contemplated, including ethynyl-, propynyl-, and butynyl-. Exemplary substituents include —OH and —OR', wherein R' is a $C_{1-4}$ alkyl. Table 1 set forth below also describes contemplated alkynyls.

Within the definition of R generally and with respect to $R^1$ and $R^2$ in the general formula referenced above, the term "aryl" is meant to have its art-recognized meaning. Substituted, unsubstituted, and multiple ring aryl groups are particularly contemplated, including benzyl-, ethylbenzyl-, phenyl-, xylene substituents, toluene substituents, sytrene substituents, and naphthalene substituents. Table 1 set forth below also describes contemplated aryls.

More particularly, the spacer unit may be —$(CH_2)_3NH(CH_2)_2NH(CH_2)_3$—; —$(CH_2)_3NH(CH_2)_3$—; —$CH_2CH_2CH_2NHCONHCH_2CH_2CH_2$—; and —$OC_6H_4N$=$NC_6H_4O$—where R=alkyl, alkenyl, alkynyl, or aryl, as defined above, or combinations thereof. Indeed, R may be the same moiety or different moieties.

Optionally, the glass composite material of the present invention may further comprise an acid or base catalyst. Examples include HCl, $HNO_3$, $H_2SO_4$, $HClO_4$, NaOH, KOH, $NH_4OH$, $NH_3$, $NH_2OH$, $C_5H_5N$, $C_6H_5NH_2$, and combinations thereof.

The glass composite material of the present invention may further comprise at least one additive associated with imparting a desired property to the glass composite material. Indeed, use of two or more additives is contemplated to be within the scope of the present invention. Such properties are described below in the Laboratory Examples. Examples of the additive include, but are not limited to, $R_nSi(OR)_{4-n}$ (where R=alkyl, alkenyl, alkynyl, or aryl, as defined above and n=1 to 20, preferably n=1 to 3) precursors; photoactive and photoresponsive molecules; dyes; anionic and/or cationic molecules; negatively/positively charged polymers; metal ions or complexes thereof; redox-active molecules; bioactive molecules; and biologically derived molecules, including proteins, enzymes, peptides, nucleotides, DNA, RNA, and cellular components.

More particularly, at least one of the additives may comprise $(OR)_3Si$—$CH_2CH_2CH_2NHCH_2CH_2NH_2$; $(OR)_3Si$—$CH_2CH_2C_6H_4CH_2NHCH_2CH_2NH_2$; $(OR)_3Si$—R; $(OR)_3Si$—$CH_2(CH_2)_{16}CH_3$; $(OR)_2Si$—$(R)_2$; $(OR)_3Si$—$CH_2CH_2CH_2NHCH_2CH_2NHCH_2CH_2NH_2$; $(OR)_3Si$—$CH_2CH_2CH_2N((COO-Na+)CH_2CH_2N(COO-Na+)_2$; $(OR)_3Si$—$CH_2CH_2CH_2SH$; $(OR)_3Si$—$CH_2CH_2CH_2OCH_2CH_2OCH_3$; $(OR)_3Si$—$CH_2CH_2C_5H_4N$; $(OR)_3Si$—$CH_2CH_2CH_2NOC$; $(OR)_3Si$—$CH_2CH_2CH_2COOR$; $(OR)_3Si$—ROH; $(OR)_3Si$—RCOOH; $(OR)_3Si$—RCHO; $(OR)_3Si$—RCOR; $(OR)_3Si$—$CH_2Cl$; $(OR)_3Si$—$CH_2CH_2CH_2C_6H_{12}O_5CONH$; $(OR)_3Si$—$CH_2CH_2C_5H_4S$; $(OR)_3Si$—$CH_2CH_2C_5H_4O$; and $(OR)_3Si$—$(CH_2)_nX$ where (X=—F, —Cl, —Br, —I), and (n=1 to 20). In each example, where R=alkyl, alkenyl, alkynyl, or aryl, as defined above, or combinations thereof, and R may be the same moiety or different moieties.

Alternatively, at least one of the additives may comprise carbohydrates such as monosaccharides (e.g., glucose and fructose), disaccharides (e.g., sucrose, maltose, lactose) and/or polysaccharides (e.g., starch, cellulose); a photoactive spiropyran molecule such as 1'(2-carboxyethyl)-6-nitroBIPS; and/or a photoresponsive molecule, such as flavin mononucleotide (FMN), β-nicotinamide adenine dinucleotide reduced form (NADH), bacteriorhodopsin, 8-hydroxy-1,3,6-pyrenetrisulfonic acid trisodium salt, luminol (5-amino-2,3-dihydro-1,4-phthalazinedione), bis-N-methylacridinium nitrate (N,N'-dimethyl-9,9'biacridinium dinitrate, lucigenin), and fluorescein and/or its sodium salt ($C_{20}H_{12}O_5$ and/or $C_2OH_{10}O_5Na_2$).

Further, at least one of the additives may comprise a transition metal ion, such as V, Cr, Mn, Fe, Ru, Co, Ni, and Cu, or a complex thereof. At least one of the additives may comprise an organic polymer poly(acrylic acid); an organic polymer poly(itaconic acid); or an organic polymer poly(ethylene glycol) or combinations thereof.

TABLE 1

Additional Representative Members for R when used generally, and with respect to $R^1$ and $R^2$ in the general formula listed above

| | | | |
|---|---|---|---|
| n-$(CH_2)_2CH_3$ | n-$(CH_2)_3CH_3$ | $CH(CH_3)_2$ | $CH_2CH(CH_3)_2$ |
| $CH(CH_3)CH_2CH_3$ | n-$O(CH_2)_2CH_3$ | n-$O(CH_2)_3CH_3$ | $OCH(CH_3)_2$ |
| $OCH(CH_3)_2$ | $OCH_2CH(CH_3)_2$ | $OCH(CH_3)CH_2CH_3$ | OPh* |
| $OCH_2CH_2OH$ | $OCH_2CH_2OCH_3$ | n-$CH_2(CH_2)_{16}$—$CH_3$ | |

*Ph = phenyl

Synthesis of Glass Composite Material

Though the prior organic "smart" material systems have been intensively studied, they require a time-consuming, multi-step synthesis process with lower yields, using harsh conditions unsuitable for the encapsulation of biomolecules. In comparison, sol-gel materials of the present invention have the following advantages over the prior art preparative method and quality of the organic polymeric materials (Hench et al. (1990) *Chemical Reviews* 33–72):

1. Low temperature preparation.
2. High purity because of the quality of the available precursors.
3. Tailoring of textural properties of the product, including surface area and pore size distribution.
4. Optical transparency above 300 nm.
5. Ability to control structure and composition at a molecular level.
6. Retention of solvent phase within the interconnected porous network.
7. Ability to introduce several components in a single step.
8. High homogeneity in multi-component glasses.
9. Flexibility in producing glasses of varying compositions.
10. Simple preparation and working conditions.
11. Ability to make different product (gel) forms, like bulk, thin film, or powdered forms.
12. Ability to impose kinetic constraints on a system and thereby stabilize metastable phases.

The inorganic polymeric network prepared by the sol-gel method progresses through the aggregation of small colloids or addition of low molecular weight particles to larger ones. Hence, a source of low molecular weight silica monomers or oligomers is available even at an advanced stage of polymerization, unlike the organic polymers which evolve through the formation of dimers, trimers, and linear chains, which cross-link to form the gel. High molecular weight silica oligomers are more stable than low molecular weight, and provide excellent conditions for "necrophilic" growth of large particles, as described by Lev et al. (1995) *Analytical Chemistry* 67, 1:22A–30A. Biomolecules cannot be encapsulated in organic polymers in the initial step since they will denature under the conditions in which the polymerization is executed. In addition, polymerization is a multi-step process with relatively much lower yield as compared to the sol-gel method.

Transparent, glassy materials with $SiO_2$ framework are typically made by hydrolysis and condensation of alkoxy silane precursors (for example, TMOS) at room temperature, according to the following general reactions:

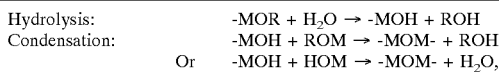

| Hydrolysis: | | -MOR + $H_2O$ → -MOH + ROH |
|---|---|---|
| Condensation: | | -MOH + ROM → -MOM- + ROH |
| | Or | -MOH + HOM → -MOM- + $H_2O$, | where M=a silicon atom (Si). These materials have both rigid and wet properties because of entrapment of water within the Si—O—Si network. This makes it possible to physically encapsulate organic molecules and biomolecules, including proteins and enzymes, inside the glass without requiring a functional modification of the biomolecules. Biomaterials with numerous applications, including application as biosensors, bioelectronic devices, and the like can thus be produced.

Designing at the molecular level by the appropriate choice of the starting alkoxide precursors $[M(OR)_n]$ helps in controlling the property of the resulting composite material at the macro level. More particularly, according to the present invention, covalent modification of the alkoxy silanes at the molecular level can modify the structural rigidity and properties of the resulting composite material. One of the alkoxy groups can be replaced by another group having hydrophobic/hydrophilic domains, metal ion-coordinating domains, charged functionalities, N—, O—, S—, etc., containing ligands, and other domains as described above. The resulting materials possess modified properties as compared to the parent $SiO_2$, and show structural variations with respect to external stimuli like salt, solvents, temperature, pH, electric field, etc. These variations can be applied to make useful devices like sensors, actuators, transducers, and smart materials. Since the "sensing-actuating" mechanism is an intrinsic property of the gel, the resulting devices are self-sufficient, simple, self-sustaining, and virtually fail proof.

A preferred example of the porous glass composite material of the present invention was synthesized as a gel according to the following procedure. The preferred gel is referred to herein as an "enTMOS" gel, in that it was designed to include a trimethoxysilyl (TMOS) component and an ethylenediamine (en) spacer unit. The enTMOS gel was made by mixing equivolume of Bis-{(trimethoxysilyl)-propyl}-ethylenediamine (available from Gelest, Inc., Tullytown, Pa.—this product is basic and hence, the gelation reaction is self-catalyzed, that is, the addition of base as a catalyst is not required) and water. The gelation time for the composite material was 1–2 minutes. The gel was obtained in monolith form by pouring the appropriate volumes of the sol in a 4 mL cuvette. Alternatively, thin films can be obtained by dip coating, spin coating, or spray coating. The monolith gel was kept for drying for 2 days, and then subjected to different environmental factors like varying salt concentration, solvents, pH, electric field, etc., to observe the "smart response" of the material to its environment. The blank enTMOS gel was characterized by IR, UV (FIG. 1*b*), and TEM techniques.

As seen in FIG. 1*b*, a tail in the UV spectra of the enTMOS material at about 380–400 nm indicates that the pore size of this gel, with its two propyl groups and an ethylenediamine spacer group, is much bigger than the parent TMOS gel, which just has a Si—O—Si network (FIG. 1*a*). This makes the enTMOS gel hold more water than the TMOS gel and thus, be more responsive to stimuli. The presence and different nature of the groups in the enTMOS precursor also make the gel have a certain ratio of hydrophobic and hydrophilic composition whereby it responds in a particular way when subjected to different environmental stimuli (FIG. 11).

LABORATORY EXAMPLES

The following Laboratory Examples have been included to illustrate preferred modes of the invention. Certain aspects of the following Laboratory Examples are described in terms of techniques and procedures found or contemplated by the present inventors to work well in the practice of the invention. These Laboratory Examples are exemplified through the use of standard laboratory practices of the inventors. In light of the present disclosure and the general level of skill in the art, those of skill will appreciate that the following Laboratory Examples are intended to be exemplary only and that numerous changes, modifications and alterations can be employed without departing from the spirit and scope of the invention.

The enTMOS gel prepared as described above was subjected to the following stimuli:

Example 1

Solvent Effect

The gel was made by mixing 1 mL each of the enTMOS precursor and water to form a polymeric gel (by hydrolysis and condensation) in a monolith form. The gel was weighed and then immersed in 10 mL of different solvents of varying polarity for 2 days. The solvents used were carbon tetrachloride, toluene, benzene, diethylether, cyclohexanol, acetone, 1-propanol, ethanol, methanol, and water. The gel was weighed again to observe any change in weight (FIG. 2).

The observed trend (FIG. 2) of a greater decrease in the weight of the gel when exposed to non-polar solvents, and an increase in weight of the gel in polar solvents, complies with the fact that in polar solvents the hydrogen bonding between the water molecules, and the hydrophilic part of the gel, i.e., the amine groups and the oxygen atom in the polymeric backbone, is enhanced. This enhancement results in retention of water molecules and some of the polar solvent molecules in the pores of the gel, thereby increasing the weight of the gel. While in non-polar solvents, the hydrogen bonding is broken, resulting in the expulsion of water from the gel thereby decreasing the weight of the gel. When the gel is subjected to different solvents of varying polarity, the water molecules inside the gel are pushed out or pulled into the gel because of breaking or strengthening of the hydrogen bonds, respectively. The graphs plotted between the weight of the gel and solvent polarity show a linear relationship.

Example 2 pH Effect

The monolith gel made by the process described above was subjected to 10 mL solutions of different pH to note any change in the gel. pH solutions of 4.5, 7.0, 8.0, and 11.0 were used. Different pH conditions resulted in a change in the pore size of the gel. Under acidic conditions the amine groups were protonated. As a result, there was a repulsion between positive charges, leading to an increase in the size of the pores, which made the gel soft and slightly opaque. Under basic conditions, however, there was a decrease in the pore size because of the deprotonation of the amine groups, resulting in shrinkage of the pores.

Example 3

Temperature Effect

The enTMOS gel made by the process described above was dried for 2 days and weighed. It was then immersed in water and subjected to two different extreme temperatures (80° C. and 4° C.) for 15 minutes at each temperature, and weighed to observe any change in the weight. All the various temperatures studied were 80° C., 70° C., 50° C., and 40° C. for the higher side, and 20° C. and 4° C. for the lower side. The influence of temperature variation between 4° C. and 80° C. on weight change is shown in FIG. 3b. The enTMOS precursor was also mixed with other precursors like methyltrimethoxysilane (MTMOS), and 3-aminopropyltrimethoxysilane in different ratios of 20:80 and 80:20 (enTMOS:others), to see any variation in the weight change during the above thermal experiment from the plain enTMOS gel (FIG. 4).

The reversible cycle seen in FIG. 3b shows that subjecting the gel to a high temperature (80° C.) for 15 min. resulted in breaking of the hydrogen bond between the water and the hydrophilic portion of the gel. This expels the water out of the gel, leading to a decrease in its weight. At a low temperature (4° C.), the hydrogen bonding with water molecules was restored in the gel, resulting in an increase in the weight of the gel (FIG. 3a). This reversible process was established for as many as 15 cycles. However, it is possible that the material will exhibit a reversible response for a large number of cycles.

As seen in FIG. 4, the effect of mixing the enTMOS precursor with the methyltrimethoxysilane (MTMOS) precursor, which is more hydrophobic than enTMOS, was that a lesser % weight change was observed as compared to the plain enTMOS gel. Particularly, the gel of 20% MTMOS and 80% enTMOS composition released more water than the gel with 80% MTMOS and 20% enTMOS composition. In line with the gel with greater hydrophilic character releasing more water or showing greater weight change, the gel with 80% enTMOS and 20% AMPTMOS (3-aminopropyltrimethoxysilane) composition released more water or showed greater % weight change than the plain enTMOS gel.

This observation shows that the greater the hydrophilic character of the gel, the more water retained by the gel through hydrogen bonding. Therefore, at a higher temperature, when the hydrogen bonding is broken, more water is pushed out of the gel. If the gel has a more hydrophobic % composition, it holds less water through hydrogen bonding, and hence, a lesser % weight change is seen in the gel with greater hydrophobic composition.

Example 4

Introduction of Metal Ions

The enTMOS gel was kept in contact with a fixed volume of different metal ion solutions of a particular concentration such that the ratio of the metal ion to ethylenediamine in the precursor was 1:3. The gel was then monitored for its intake of the metal ions. The metal ions studied were $Cu^{(+2)}$ and $Co^{(+2)}$ ions. The gel was also kept in contact with a mixture of $Cu^{(+2)}$ and $Co^{(+2)}$ ions to monitor any preferred intake by the gel. The mixture of $Cu^{(+2)}$, $Co^{(+2)}$ was passed through a column packed with powdered enTMOS, and the eluted fractions were analyzed with atomic absorption spectroscopy (MS).

The amine groups in the gel were observed to act as coordinating ligands for different metal ions. Therefore, the enTMOS gel changes its color to purple or blue, respectively, on taking in $Cu^{(+2)}$ or $Co^{(+2)}$ ions. Spectroscopic measurements were done to monitor the color change (FIG. 12). The MS results show that in a mixture of $Cu^{(+2)}$ and $Co^{(+2)}$ ions, the gel has a preference for the intake of $Cu^{(+2)}$ ions. Though 100% separation was not achieved, the first fraction eluted with water had 30% more of $Co^{(+2)}$ ions than $Cu^{(2+)}$ ions, and the second fraction eluted with ethylenediamine tetraacetic acid (EDTA) had 20% more of $Cu^{(2+)}$ ions.

Example 5

Encapsulation of Biomolecules

Different biomolecules (proteins) like cytochrome c, (Cyt c), myoglobin (Mb), and hemoglobin (Hb) were encapsulated in enTMOS gels by making the gel with equivolume of enTMOS precursor and the solution of the proteins of a particular concentration. The stability of the encapsulated proteins was monitored using UV spectroscopy (FIGS. 5a and 5b). Subjecting the gel having the encapsulated proteins to acidic conditions resulted in the release of the proteins due to the enlargement of the pores of the gel. The solution receiving the released proteins was monitored hourly by absorption spectroscopy (FIGS. 6a and 6b).

The enTMOS gel was kept in contact with a mixture of proteins, Cyt c and Mb, and Cyt c and Hb, for two days to observe any preferred intake of a particular protein by the enTMOS gel on the basis of the charge on the proteins (FIGS. 7 and 9).

Stability of biomolecules in the gel: Absorption-spectroscopic studies show that the proteins encapsulated in the gel were found to be as stable as they were in the solution, indicating that the proteins retained their conformation in the gel (FIGS. 5a and 5b).

Release of biomolecules: The spectra (FIGS. 6a and 6b) show the data collection of the hourly release of the proteins from the gel. These data indicate that, on subjecting the gel having the encapsulated proteins to acidic conditions, the pore size in the gel increased through protonation of the amine groups, thereby releasing the encapsulated proteins.

Protein separation on the basis of charge: FIG. 7 shows that on subjecting the gel to a mixture of Cyt c (+8 charged) and Mb or Hb (+2 charged), the gel selectively picked up the less positively charged Mb or Hb (FIG. 9) rather than the Cyt c. FIG. 8 shows that there was an increase in the intake ratio Mb/Cyt c when a gel made under neutral conditions, or a gel made under acidic conditions (i.e., gel made with pH 1 solution) was subjected to an equivimolar concentration of Cyt c and Mb. A subsequent decrease in the Mb/Cyt c ratio was observed when a gel made under basic conditions (i.e., gel made with pH 11 solution) was subjected to the same protein mixture. This is because the enTMOS gel was positively charged under the conditions in which it was made, i.e., under acidic or neutral conditions due to the protonation of the amine groups, and so it repelled the intake of the more positively charged biomolecule (Cyt c). Thus, the composite material of the present invention can be used to separate proteins and other charged biomolecules on the basis of charge.

Example 6

Influence of Electrical Potential

The enTMOS gel was made into a tweezers shape by keeping a thin piece of non-glassy material (PVC) in the middle of the sol when it was in the process of gelation. This piece was then removed carefully after the gel formed. The tweezers-shaped gel was then immersed in sodium acetate buffer solution (pH 4.5) for 5–6 hours. A potential of 6V was then applied to the gel for 15 minutes and reversed thereafter for the next 15 minutes (FIG. 10).

FIG. 10 shows that the arms of the tweezers-shaped enTMOS gel can be moved by applying potential. The tweezers were kept in an acetate buffer (pH 4.5). On applying the potential to the tweezers containing acetate ions, the arms moved back by 15%, and on reversing the potential, the arms moved closer to each other by the same amount. This movement of the arms is caused by the movement of ions inside the gel with respect to potential. This also has been observed to be reversible for a number of cycles.

Example 7

Ionic Environment

The tweezers-shaped gel was placed in different ionic solutions of 0.1 M concentration of sodium acetate buffer (pH 4.5), sodium chloride, magnesium sulfate, potassium phosphate (tribasic) and calcium carbonate.

The arms of the tweezer-shaped enTMOS gel kept in sodium acetate buffer moved closer to each other by 50% as compared to 11% in $MgSO_4$, 6% in NaCl, and no change in $K_3PO_4$. On keeping the tweezer-shaped gel in water, the acetate ions were removed, and the arms of the tweezer separated by 33%.

Example 8

Mechanical Pressure

The enTMOS gel was prepared as described above, and then powdered. The powdered gel was filled into a syringe, and mechanical pressure was applied to this syringe to bring the piston to the powder level. The syringe was then placed overnight in 6M hydrochloric acid.

The piston in the syringe containing the powdered enTMOS gel, when put in 6M HCl, was pushed back due to the expansion of the pore size of the gel. This is because of the repulsion between the positive charges caused by the protonation of the amine groups with HCl.

APPLICATIONS OF THE GLASS COMPOSITE MATERIAL

Materials for separation: The glass composite material of the present invention contains internal charges on the pores, and therefore can be used for separation of metal ions and charged molecules, including proteins and enzymes. The selectivity for metal ions derives from differences in metal ion coordination by the ligating groups within the glass composite material. While the separation of molecules is based on differences in electrostatic interactions with the matrix, the material can be used for separation in bulk form as well as in powdered form. The glass composite material of the present invention, in powdered form, can thus be used as a column packing material for the separation of metal ions and charged biomolecules, like enzymes and proteins, because of their different extent of electrostatic interactions with the gel.

The process of sol-gel facilitates the encapsulation of organic/biomolecules in the beginning of the process. This can be used to imprint a gel comprising the glass composite material of the present invention with a particular molecule of interest. The imprinted molecule can then be released from the gel by subjecting it to acidic conditions, thereby creating impressions of the imprinted molecule. This gel can be used as a sensor for the particular molecule with which it was imprinted.

Since the glass material can be tailored to have certain properties by the appropriate choice of the starting materials, the material can be used to selectively separate some metal ions from others by incorporating ligands/coordination domains which are specific for them in the starting precursor, thereby making ion-selective sensors.

The porous glass composite material of the present invention can thus be utilized in shape-selective and charge-selective chromatographic separation including separation of metal ions, organic and/or inorganic complexes, proteins, enzymes, antibodies, and other biologically derived molecules.

Shape-memory materials: The porous glass composite material of the present invention undergoes changes in pore sizes with respect to external stimuli such as pH, salt, solvent, temperature, electric field, and mechanical pressure. Restoring the environmental conditions returns the material to its original shape. This feature can be used for different applications based on shape memory. For example, the change in shape with respect to temperature can be used for designing mechanical devices for energy storage.

The changes in shape with respect to mechanical pressure can also be used for designing microsyringes for delivering very small amounts, e.g. less than picoliter (pL) amounts. Micropumps can be designed in a similar manner. (FIG. 13).

The materials eject solvent when heated, and therefore can be used in fabricating temperature-directed syringes. Because of the observed response to temperature changes, the porous glass composite material of the present invention can be thus also used in fabricating thermally sensitive devices for shape-memory, thermal data storage, and thermomechanical devices.

The porous glass composite material of the present invention can thus also be used in fabricating optical devices for optical-memory, optical data storage, and optomechanical devices.

Electromechanical actuators: The changes in shape with respect to electric field observed in the glass composite material of the present invention may be used for designing robotics fingers that bend or flex under an applied potential. Also, using this response an electric field, electromechanical actuators can be prepared that act as mechanical switches with respect to an applied potential as part of microelectromechanical devices. (FIG. 13).

The porous glass composite material can thus be used in fabricating electromechanical devices based on changes in shape under an applied potential. For example, the movement shown by the arms of the enTMOS tweezers-shaped gel in different ionic environment can be used in making devices like microsyringes, micropumps, etc. (FIG. 13).

Controlled drug delivery: The glass composite material of the present invention swell or shrink with respect to change in temperature, pH, solvent, salt, ionic species, metal ions, chemical species, mechanical pressure, electrical potential, light, and ultrasonic sound. This feature can be used for controlled drug delivery. The drug (biological or nonbiological) can be encapsulated in the glass composite material of the present invention under ordinary conditions and then can be released under a different pH. For example, an orally ingested capsule made from the glass composite material of the present invention (containing a drug), will release the drug in the stomach where low pH conditions exist. Thus, the feature of absorption and release of biomolecules and organic molecules from the glass composite material of the present invention with respect to pH and/or salt concentrations can be used for controlled drug delivery system.

The porous glass composite material can thus also be utilized in the encapsulation of biological molecules, including growth hormones, proteins, enzymes, peptides, nucleotides, DNA, RNA, and cellular components.

Controlled biocatalysis: The change in pore sizes provided by the porous glass composite material of the present invention may be used to change an enzymatic reaction. Enzymes encapsulated in the material can react with an external substrate molecule when the pore sizes are larger so that the substrate molecules can diffuse inwardly. Making the pores smaller with respect to an external stimulus (pH, solvent, electric field, pressure, etc.) will prevent diffusion of reactants, thereby stopping catalytic reaction. The reaction may be started again by removing the stimulus.

The porous glass composite material of the present invention can also be used to provide a solid medium for any biocatalytic reaction. Such materials can be useful in catalyzing reactions under conditions where the use of liquid phase is undesirable. The porous glass composite material of the present invention can thus be used as means for design of controlled biocatalysts using an externally applied stimulus including, but not limited to temperature, pH, solvent, salt, ionic species, metal ions, chemical species, mechanical pressure, electrical potential, light, and ultrasonic sound.

The porous glass composite material of the present invention can thus also be utilized in designing biosensors, biotransducers, and bioactuators. More particularly, the porous glass composite material of the present invention can be utilized in designing electrochemical biosensors based on electron transfer from the encapsulated biologically derived molecule including proteins, enzymes, antibodies, DNA, RNA, or any combination thereof.

Tissue replacement materials: Suitable peptide/polyamino acids can be synthesized and attached to the alkoxy silane precursors of the sol-gel to make a flexible, biocompatible glass composite material according to the present invention with elastic properties that can be used as a tissue replacement material.

Conducting materials: Sol-gel precursors like enTMOS can be modified covalently or physically by incorporating organic conducting polymers like polyaniline, polypyyrole, polythiophene, etc., to convert the original, insulating $SiO_2$ material into a conducting glass composite material according to the present invention.

Summarily, suitable applications for the porous glass composite material of the present invention include applications as materials for chromatography; as time-release controlled drug delivery materials; as materials for externally controlled (bio)catalysis; as thermomechanical actuators; as micromechanical devices; as electromechanical devices; as materials for stabilizing biological molecules; as biosensor materials; as shape-memory materials; and as environmentally sensitive materials.

The present "smart" materials technology for similar applications is based on using organic polymeric materials. Biological incompatibility of organic polymers has been identified for in vivo applications. The organic polymeric materials require presence of organic solvents for swelling/shrinkage, and therefore mostly preclude usage in biomedical drug delivery applications. The encapsulation of biological molecules in the organic polymers is carried during post-synthesis steps, as high temperatures are required for preparation of these polymers. In addition, the synthesis reactions for organic polymers are multi-step, produce small yields and require large amounts of precursors and other chemicals, which raises the overall cost of manufacture.

On the other hand, the sol-gel based glass composite materials of the present invention can be prepared using a one step route, and are prepared from inexpensive precursors. The sol-gel process can be carried out at room temperature or at a lower temperature (such as 4° C., the standard temperature for most refrigerators), which enables direct encapsulation of thermally unstable molecules during the synthesis stages.

The large pore sizes of the sol-gel based glass composite materials of the present invention are also conducive to encapsulation/release of large molecules, including enzymes and antibodies (molecules up to 65 KDa can be easily encapsulated/released). These materials are ideally suited for controlled delivery in immunotherapy based on high molecular peptide drugs. Similarly, the enhanced stability of encapsulated systems is also useful for delivery of growth hormones and other biogenic substances with marginal thermal stabilities. Prior art organic polymer-based materials have smaller pores and thus, are not suitable for encapsulation of larger molecules.

Indeed, generally, there are no limitations on the commercial synthesis and applications of the glass composite materials of the present invention. The materials are prepared by simple hydrolysis of a modified alkoxosilane precursor. The glass composite materials of the present invention are based on inorganic silica glasses, and are cheaper, durable, mechanically stable, and optically transparent. The sol-gel processes by which these materials are prepared are already used in industry for commercial large-scale manufacture. The glass composite materials of the present invention are therefore synthesized easily in a one-step process which can be readily scaled for industrial preparations.

The sol-gel process is suitable for preparing a variety of structural modifications of the precursor molecules and thus, based on the same parent material, a series of modified materials with predetermined properties can be designed. Prior art polymer-based methods are multi-step and few structural modification pathways are available.

The glass composite materials of the present invention are produced in different shapes and geometries, including solid monoliths of variable dimensions, films, coatings, and powders. The overall synthesis process is on the time scale of minutes, and generally, the materials can be used after a day of aging. The tailored hydrophobic/hydrophilic properties of the materials enable encapsulation/release of polar as well as nonpolar molecules from aqueous systems. This feature is important for in vivo drug delivery, as the presence of an aqueous environment is a strict requirement in living systems. Finally, these materials are suited for encapsulation of biological molecules. Encapsulation of the biological molecules is by a physical means and therefore does not lead to denaturation. Prior art polymer-based materials are not highly efficient for bioencapsulation as they lead to substantial denaturation.

REFERENCES

The references listed below as well as all references cited in the specification are incorporated herein by reference to the extent that they supplement, explain, provide a background for or teach methodology, techniques and/or compositions employed herein.

Aegertu, *Structure and Bonding*, 85:149–194 (1996).
Dave et al., *Analytical Chemistry*, 66:1120A–1127A (1994).
Dong et al., *Journal of Controlled Release*, 13:21–31 (1990).
Feil et al., *Journal of Membrane Science*, 64:283–294 (1991).
Gehrke, S. H., *Advances in Polymer Science*, 110:80–144 (1993).
Hench et al., *Chemical Reviews*, 33–72 (1990).
Hoffman et al., *Journal of Controlled Release*, 4:213–222 (1986).
Hu et al., *Science*, 269:525–527 (July 1995).
Kim, Cherng-ju, *ChemTech*, 36–39 (August 1994).
Lev et al., *Analytical Chemistry*, 67, 1, 22A–30A (1995).
Nagasaki et al., *ChemTech*, 23–29 (March 1997).
Okano et al., *Journal of Controlled Release*, 11:255–265 (1990).
Osada et al., *Progress in Polymer Science*, 18:187–226 (1993).
Osada et al., *Scientific American*, 82–87 (May 1993).
Rossi et al., *Journal of Intelligent Material System and Structure* 3:75–95 (1992).
Wolfbeis et al., *Structure and Bonding*, 85:51–98 (1996).
Yoshida et al., *Nature*, 374:240–242 (Mar. 16, 1995).

It will be understood that various details of the invention may be changed without departing from the scope of the invention. Furthermore, the foregoing description is for the purpose of illustration only, and not for the purpose of limitation—the invention being defined by the claims.

What is claimed is:

1. A porous glass composite material comprising a gel that comprises water and a polymeric network comprising at least one alkoxosilane derivative, the network having a group of alterable charge, a hydrophobic group and a hydrophilic group, each group being a part of the least one alkoxosilane derivative.

2. The porous glass composite material of claim 1, further comprising a catalyst that is an acid catalyst or a base catalyst.

3. The porous glass composite material of claim 2, wherein the catalyst is selected from the group consisting of HCl, $HNO_3$, $H_2SO_4$, $HClO_4$, NaOH, KOH, $NH_4OH$, $NH_3$, $NH_2OH$, $C_5H_5N$, $C_6H_5NH_2$, and combinations thereof.

4. The porous glass composite material of claim 1, further comprising, entrained within the gel, an additive for imparting to the glass composite material a desired functional property.

5. The porous glass composite material of claim 4, comprising, entrained within the gel, two or more additives for imparting to the glass composite material a desired functional property.

6. The porous glass composite material of claim 4, wherein the additive is an alkoxosilane precursor having the general formula $R_nSi(OR)_{4-n}$, wherein R is the same or different and is hydrogen, unsubstituted branched and unbranched $C_{1-20}$-alkyl, substituted branched and unbranched $C_{1-20}$-alkyl, unsubstituted branched and unbranched $C_{1-20}$-alkenyl, substituted branched and unbranched $C_{1-20}$-alkenyl, unsubstituted branched and unbranched $C_{1-20}$-alkynyl, substituted branched and unbranched $C_{1-20}$-alkynyl or substituted, unsubstituted, and multiple ring aryl group, and n=1 to 3.

7. The porous glass composite material of claim 4, wherein the additive is an alkoxosilane precursor selected from the group consisting of $(OR)_3Si$—$CH_2CH_2CH_2NHCH_2CH_2NH_2$; $(OR)_3Si$—$CH_2CH_2C_6H4CH_2NHCH_2CH_2NH_2$; $(OR)_3Si$—R; $(OR)_3Si$—$CH_2(CH_2)_{16}CH_3$; $(OR)_2Si$—$(R)_2$; $(OR)_3Si$—$CH_2CH_2CH_2NHCH_2CH_2NHCH_2CH_2NH_2$; $(OR)_3Si$—$CH_2CH_2CH_2N((COO$—$Na+)CH_2CH_2N(COO$—$Na+)_2$; $(OR)_3Si$—$CH_2CH_2CH_2SH$; $(OR)_3Si$—$CH_2CH_2CH_2OCH_2CH_2OCH_2$; $(OR)_3Si$—$CH_2CH_2C_5H_4N$; $(OR)_3Si$—$CH_2CH_2CH_2NCO$; $(OR)_3Si$—$CH_2CH_2CH_2COOR$; $(OR)_3Si$—ROH; $(OR)_3Si$—RCOOH; $(OR)_3Si$—RCHO; $(OR)_3Si$—RCOR; $(OR)_3Si$—$CH_2Cl$; $(OR)_3Si$—$CH_2CH_2CH_2C_6H_{12}O_5CONH$; $(OR)_3Si$—$CH_2CH_2C_5H_4S$; $(OR)_3Si$—$CH_2CH_2C_5H_4O$; and $(OR)_3Si$—$(CH_2)_nX$ wherein X=—F, —Cl, —Br or —1 and n=1 to 20, and R is hydrogen, unsubstituted branched and unbranched $C_{1-20}$-alkyl, substituted branched and unbranched $C_{1-20}$-alkyl, unsubstituted branched and unbranched $C_{1-20}$-alkenyl, substituted branched and unbranched $C_{1-20}$-alkenyl, unsubstituted branched and unbranched $C_{1-20}$-alkynyl, substituted branched and unbranched $C_{1-20}$-alkynyl, substituted, unsubstituted, and multiple ring aryl groups, and wherein R is the same or different.

8. The porous glass composite material of claim 4, wherein the additive is selected from the group consisting of photoactive molecules, photoresponsive molecules, dyes, negatively charged polymers, positively charged polymers, metal ions or complexes thereof, redox-active molecules, biologically active molecules, biologically derived molecules and combinations thereof.

9. The porous glass composite material of claim 8, wherein the biologically active molecules are selected from the group consisting of carbohydrates, proteins, enzymes, peptides, nucleotides, DNA, RNA, cellular components and combinations thereof.

10. The porous glass composite molecule of claim 9, wherein the carbohydrate is selected from the group consisting of monosaccharides, disaccharides, polysaccharides and combinations thereof.

11. The porous glass composite molecule of claim 8, wherein the additive is a photoactive spiropyran molecule.

12. The porous glass composite molecule of claim 11, wherein the photoactive spiropyran molecule is 1'(2-carboxyethyl)-6-nitroBIPS.

13. The porous glass composite molecule of claim 8, wherein the additive is a photoresponsive molecule selected from the group consisting of flavin mononucleotide (FMN), β-nicotinamide adenine dinucleotide reduced form (NADH), bacteriorhodopsin, 8-hydroxy-1,3,6-pyrenetrisulfonic acid trisodium salt, luminol (5-amino-2,3-dihydro-1,4-phthalazinedione), bis-N-methylacridinium nitrate (N,N'-dimethyl-9,9'biacridinium dinitrate), fluorescein or its sodium salt ($C_{20}H_{12}O_5$ and/or $C_{20}H_{10}O_5Na_2$), and combinations thereof.

14. The porous glass composite material of claim 8, wherein the metal ion is a transition metal ion.

15. The porous glass composite material of claim 14, wherein the transition metal is selected from the group consisting of V, Cr, Mn, Fe, Ru, Co, Ni and Cu.

16. The porous glass composite material of claim 8, wherein the additive is selected from the group consisting of a polymer poly(acrylic acid), a polymer poly(itacnic acid), a polymer poly(ethylene glycol) and combinations thereof.

17. The porous glass composite material of claim 1, wherein each of the at least one alkoxosilane derivative is a derivative of an alkoxosilane having the general formula $(OR^1)_3Si\text{-spacer-}Si(OR^2)_3$, wherein $R^1$ and $R^2$ are the same or different and are selected from the group consisting of hydrogen, unsubstituted branched and unbranched $C_{1-20}$-alkyls, substituted branched and unbranched $C_{1-20}$-alkyls, unsubstituted branch and unbranched $C_{1-20}$-alkenyls, unsubstituted branched and unbranched $C_{1-20}$-alkenyls, unsubstituted branched and unbranched $C_{1-20}$-alkynyls, substituted branched and unbranched $C_{1-20}$-alkynyls, substituted, unsubstitued, and multiple ring aryl groups, and combinations thereof.

18. The pourous glass composite material of claim 17, wherein the spacer comprises a domain selected from the group consisting of charged functional groups; hydrophic groups; hydrophilic groups; and combinations thereof; wherein the domain comprises a moiety selected from a group consisting of —S, —N, —N=N—, halogen, —OR,—R—O—R, —HOOCR, —HOR wherein R is hydrogen, unsubstituted branched and unbranched $C_{1-20}$-alkyls, substituted branched and unbranched $C_{1-20}$-alkyls, unsubstituted branched and unbranched $C_{1-20}$-alkenyls, unsubstituted branched and unbranched $C_{1-20}$-alkenyls, unsubstituted branched and unbranched $C_{1-20}$-alkynyls, substituted branched and unbranched $C_{1-20}$-alkynyls, substituted, unsubstituted, and multiple ring aryl groups, and wherein R is the same or different; and combination thereof.

19. The porous glass composite material of claim 18, wherein the spacer is selected from the group consisting of $RHN(CH_2)_2NHR$, RNHR, and RNHCONHR, wherein R is hydrogen, unsubstituted branched and unbranched $C_{1-20}$-alkyls, substituted branched and unbranched $C_{1-20}$-alkyls, unsubstituted branched and unbranched $C_{1-20}$-alkenyls, substituted branched and unbranched $C_{1-20}$-alkenyls, unsubstituted branched and unbranched $C_{1-20}$-alkynyls, substituted branched and unbranched $C_{1-20}$-alkenyls, substituted, unsubstituted, and multiple ring aryl groups, and wherein R is the same or different.

20. The porous glass composite material of claim 17, wherein $R^1$ is selected from the group consisting of n-$(CH_2)_2$ $CH_3$, n-$(CH_2)_3CH_3$, —$CH(CH_3)_2$, —$CH_2CH(CH_3)_2$, —$CH(CH_3)CH_2CH_3$, —$CH_2CH(CH_3)_2$, —$CH(CH_3)CH_2CH_3$, OPh, —$CH_2CH_2OH$, —$CH_2CH_2OCH_3$, n-$CH_2(CH_2)_{16}$—$CH_3$, n-$O(CH_2)_2CH_3$, n-$O(CH_2)_3CH_3$, $OCH(CH_3)_2$, $OCH(CH_3)_2$, $OCH_2CH(CH_3)_2$, $OCH(CH_3)CH_2CH_3$, $OCH_2CH_2OH$ and $OCH_2CH_2OCH_3$.

21. The porous glass composite material of claim 17, wherein $R^2$ is selected from the group consisting of n-$(CH_2)_2$ $CH_3$, n-$(CH_2)_3CH_3$, —$CH(CH_3)_2$, —$CH_2CH(CH_3)_2$, —$CH(CH_3)CH_2CH_3$, —$CH_2CH(CH_3)_2$, —$CH(CH_3)CH_2CH_3$, OPh, —$CH_2CH_2OH$, —$CH_2CH_2OCH_3$, n-$CH_2(CH_2)_{16}$—$CH_3$, n-$O(CH_2)_2CH_3$, n-$O(CH_2)_3CH_3$, $OCH(CH_3)_2$, $OCH(CH_3)_2$, $OCH_2CH(CH_3)_2$, $OCH(CH_3)CH_2CH_3$, $OCH_2CH_2OH$ and $OCH_2CH_2OCH_3$.

22. The porous glass composite material of claim 17 wherein the spacer corresponds to the formula —$[(CH_2)_3NH(CH_2)_2NH(CH_2)_3]$—.

23. The porous glass composite material of claim 17 wherein the spacer corresponds to the formula —$[(CH_2)_3NH(CH_2)_3]$—.

24. The porous glass composite material of claim 17 wherein the spacer corresponds to the formula —$[CH_2CH_2CH_2NHCONHCH_2CH_2CH_2]$—.

25. The porous glass composite material of claim 17 wherein the spacer corresponds to the formula —$OC_6H_4N=NC_6H_4O$—.

26. A separation medium comprising the porous glass composite material of claim 1 affixed to a solid support.

27. The separation medium of claim 26, wherein the medium is a chromatographic separation medium.

28. A delivery vehicle for a bioactive agent comprising the porous glass composite material of claim 1 in a biologically compatible form and wherein the porous glass material composite further comprises a bioactive material entrapped within the network.

29. The delivery vehicle of claim 28, wherein the bioactive material is a drug.

30. The delivery vehicle of claim 28, wherein the vehicle is adapted for controlled release of the bioactive agent.

31. A biocatalyst comprising the porous glass composite material of claim 1 and an enzyme.

32. A sensor for use in detecting a predetermined variable, the sensor comprising the porous glass composite material of claim 1 exposed to an environmental stimulus associated with the predetermined variable.

33. The sensor of claim 32, wherein the environmental stimulus is selected from the group consisting of light, heat, pH change, exposure to a metal ion, electron transfer and combinations thereof, and the predetermined variable is selected from the group consisting of temperature change, optical change, pH change, presence of a metal ion, presence of a biomolecule and combinations thereof.

34. An actuator device comprising the porous glass composite of claim 1 and a prime mover operatively positioned therewith.

35. The actuator device of claim 34, wherein the porous glass composite material is adapted to move the prime mover in response to a mechanical stimulus.

36. The actuator device of claim 34, wherein the porous glass composite material is adapted to move the prime mover in response to an electrical stimulus.

* * * * *